United States Patent [19]

Foulletier et al.

[11] 4,062,849
[45] Dec. 13, 1977

[54] PERFLUOROALKYLENE QUATERNARY HETEROCYCLIC NITROGEN SALTS

[75] Inventors: Louis Foulletier, Oullins (Rhone); Jean-Pierre Lalu, La Mulatiere (Rhone), both of France

[73] Assignee: Produits Chimiques Ugine Kuhlmann, Saint-Denis, France

[21] Appl. No.: 696,727

[22] Filed: June 16, 1976

Related U.S. Application Data

[63] Continuation of Ser. No. 821,132, May 1, 1969, abandoned.

[30] Foreign Application Priority Data

May 2, 1968    France .............................. 68.150252

[51] Int. Cl.² .......................................... C07D 219/00
[52] U.S. Cl. .......................... 260/279 R; 260/239 B; 260/239 BE; 260/283 S; 260/286 Q; 260/290 HL; 260/294.8 R; 260/293.51; 260/293.85; 260/313.1; 260/326.8; 260/326.82
[58] Field of Search ................... 260/326.82, 294.8 R, 260/290 HL, 286 Q, 283 R, 279 R, 239 BE, 239 B, 313.1, 326.8, 293.51, 293.85

[56] References Cited

U.S. PATENT DOCUMENTS 3,257,407   6/1966   Brace ................................ 260/290 HL

OTHER PUBLICATIONS

Schwartz et al., Surface Active Agents and Detergents, vol. II, Interscience Pub. pp. 112-119 (1958).

*Primary Examiner*—Alan L. Rotman

[57] ABSTRACT

New compositions having the following general formula:

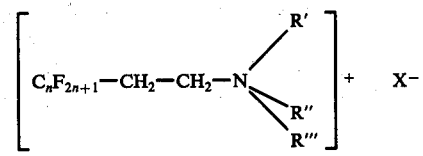

in which a. $C_nF_{2n+1}$ represents a straight or branched perfluorinated chain with $n$ being 1 and 20.

b. X⁻ is an anion such as a halogen, a sulfate, an alkyl sulfate.

Of these anions the preferred ones are halogens such as the fluoride, chloride, bromide and iodide, or sulfates such as $CH_3SO_4^-$, c. R', R" and R'" correspond to the following definitions:

1. R' is an alkyl radical containing from 1 to 8 atoms of carbons, in which event
   i. R" and R'" can be either the same as R' or different, namely, alkyl radicals containing from 1 to 8 atoms of carbon. R" and R'" can also be cycloalkyl radicals containing from 5 to 10 carbon atoms or alkenyl radicals containing from about 3 to 8 atoms of carbon, or cycloalkenyl radicals containing from 5 to 9 atoms of carbon, or ayrl radicals.
   ii. R" and R'" together make up a divalent radical linked to the nitrogen by two simple bonds such as cycloalkyl radicals containing from 4 to 9 carbon atoms, cycloalkenyl radicals containing 4 to 9 carbons, or cyclodienic radicals containing from 4 to 9 carbons.

2. R', R" and R'" make up together the remainder of an aromatic tertiary amine derived from the pyridine containing from 5 to 18 carbons. Of these aromatic tertiary amine remainders, the preferred ones are $C_5H_5$ (pyridine), $C_6H_8$ (the picolines), $C_9H_7$ (quinoline and isoquinoline), and $C_{13}H_9$ (acridine).

4 Claims, No Drawings

PERFLUOROALKYLENE QUATERNARY HETEROCYCLIC NITROGEN SALTS

This is a continuation, division, of application Ser. No. 821,132, filed May 16, 1969, now abandoned.

BACKGROUND OF THE INVENTION

Two classes of polyfluorinated quaternary ammonium salts have been described in the literature. Thus, U.S. Pat. No. 2,727,923 claims products of the formula $$[C_nF_{2n+1}-CH_2-NR_1R_2R_3]^+ X^-$$

in which n is an integer between 3 and 9. These products are obtained by reduction of the amide $$C_nF_{2n+1}-CO-NR_1R_2$$

followed by the reaction of the amine $$C_nF_{2n+1}-CH_2-NR_1R_2$$

with the compound of the formula $R_3X$. $R_1$, $R_2$ and $R_3$ are alkyl radicals containing from 1 to 5 carbons. X represents bromine, iodine, chlorine, fluorine or the hydroxyl group.

On the other hand, U.S. Pat. No. 3,257,407 claims ammonium salts of the formula $$[C_nF_{2n+1}-(CH_2)_m-NR_3R_4R_5]^+ X^-$$

in which n is between 3 and 20, m is between 3 and 30 and and $NR_3R_4R_5$ represents a radical derived from ammonia or pyridine. The patentee asserts that the quaternary ammonium salts $$[C_nF_{2n+1}-CH_2-CH_2-NR'R''R''']^+ X^-$$

cannot be synthesized from the iodides of the polyfluoroalkanes $$C_nF_{2n+1}-CH_2-CH_2I$$

because the latter are deiodohydrogenated by the tertiary amines in accordance with equation (4).

$$C_nF_{2n+1}-CH_2-CH_2-I \xrightarrow{NR'R''R'''} C_nF_{2n+1}-CH=CH_2 \quad (4)$$

SUMMARY OF THE INVENTION

This invention relates to new compositions or compounds of the following formula

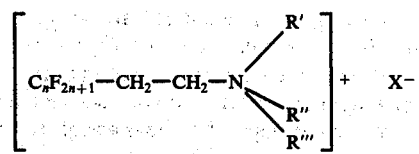

in which
a. $C_nF_{2n+1}$ represents a straight or branched perfluorinated chain with n being between 1 and 20.
b. $X^-$ is an anion such as a halogen, a sulfate, an alkyl sulfate.

Of these anions the preferred ones are the halogens such as the fluoride, chloride, bromide and iodide or of sulfates such as $CH_3SO_4^-$, c. R', R" and R'" correspond to the following definitions:
1. R' is an alkyl radical containing from 1 to 8 atoms of carbons, in which event
   i. R" and R'" can be either the same as R' or different, namely, being alkyl radicals containing from 1 to 8 atoms of carbon. R" and R'" can also be cycloalkyl radicals containing from 5 to 10 carbon atoms or alkenyl radicals containing from 3 to 8 atoms of carbon, or cycloalkenyl radicals containing from 5 to 9 atoms of carbon, or else ayrl radicals.
   ii. R" and R'" together make up a divalent radical linked to the nitrogen by two simple bonds such as cycloalkyl radicals containing from 4 to 9 carbon atoms, cycloalkenyl radicals containing 4 to 9 carbons, or cyclodienic radicals containing from 4 to 9 carbons.
2. R', R" and R'" make up together the remainder of an aromatic tertiary amine derived from the pyridine containing from 5 to 18 carbons. Of these aromatic tertiary amine remainders, the preferred ones are $C_5H_5$ (pyridine), $C_6H_8$ (the picolines), $C_9H_7$ (quinoline and isoquinoline), and $C_{13}H_9$ (acridine).

DETAILED DESCRIPTION OF THE INVENTION

The preparation of the products of the invention is carried out either by a reaction between
a. a polyfluoroalkane halide of the formula $$C_nF_{2n+1}-CH_2-CH_2-X$$

wherein X is iodine or bromine, and
b. an aromatic tertiary amine derived from the pyridine according to the following equation (1):

$$C_nF_{2n+1}-CH_2-CH_2-X + NR'R''R''' \rightarrow [C_nF_{2n+1}-CH_2CH_2-N-R'R''R''']^+ X^{31} \quad (1)$$

or by reaction between a fluorinated tertiary amine $$C_nF_{2n+1}-CH_2-CH_2-NR''R'''$$

and a compound of the formula R'X as set forth in equation (2) in which X represents iodine, bromine or an alkylsulfate such as $CH_3-SO_4-$ $$C_nF_{2n+1}-CH_2-CH_2-NR''R''' + R'X \rightarrow [C_nF_{2n+1}-CH_2-CH_2-NR'R''R'''] +X^- \quad (2)$$

These amines have been described in applicants copending applications Ser. Nos. 694,045, 694,081, 694,090 and 694,105, all filed Dec. 28, 1967 and all assigned to the assignee hereof.

The reactions represented by equations (1) and (2) are carried out with or without a solvent, and preferably without.

The polyfluorinated quaternary salts of ammonium are prepared at temperatures between 0° and 200° C. and preferably between 40° and 120° C.

It has been found, however, contrary to the assertion in U.S. Pat. No. 3,257,407, that the quaternary ammonium salts of the form $$[C_nF_{2n+1}-CH_2-CH_2-NR'R''R''']^+ X^-$$

in which NR'R"R'" represents an aromatic amine derived from pyridine, can be prepared from the iodides or bromides of polyfluoroalkanes of the form $$C_nF_{2n+1} - CH_2 - CH_2 - X$$

in which X is iodine or bromine. An example of this process is as follows:

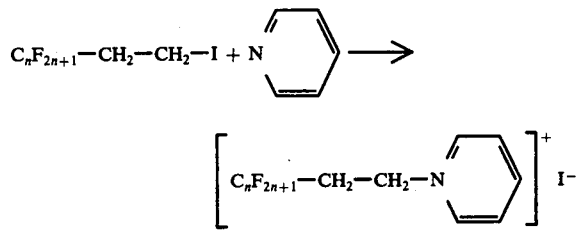

The result of this equation may appear to contradict or to be inconsistent with the method of preparing the poly fluorinated amines;

$$C_nF_{2n+1} - CH_2 - CH_2 - NR''R'''$$

described in applicants' copending applications filed Dec. 28, 1967 above cited. Indeed in those copending applications it is set forth that the polyfluorinated amines may be obtained by action of amines of the form HNR"R'" on the halides of the polyfluoroalkanes $$C_nF_{2n+1} - CH_2 - CH_2 - X$$

(X being iodine or bromine) by using a tertiary amine such as pyridine as a solvent. In fact however the polyfluoroamines of the form $$C_nF_{2n+1} - CH_2 - CH_2 - NR''R'''$$

are obtained with good yields when pyridine is used as a solvent because the competition between the amine HNR"R'" and the pyridine with respect to the halides of the polyfluoroalkanes $$C_nF_{2n+1} - CH_2 - CH_2X$$

(X being iodine or bromine) distinctly favors the amine HNR"R'".

In the general case in which the tertiary amine is not a derivative of the pyridine as hereinabove defined, the reaction with the halides of polyfluoroalkanes $$C_nF_{2n+1} - CH_2 - CH_2 - X$$

(X being iodine or bromine) does not produce quaternary ammonium salts. Rather, according to the experimental conditions employed it may either produce the olefins $$C_nF_{2n+1} - CH = CH_2$$

or it may leave the starting material unchanged. To obtain the quaternary ammonium salts $$[C_nF_{2n+1} - CH_2 - CH_2 - NR'R''R''']^+ X^-$$

it is then necessary to react a polyfluorinated tertiary amine of the formula $$C_nF_{2n+1} - CH_2 - CH_2 - NR''R''',$$

described in the above-cited U.S. applications with a compound of the formula R'X as follows:

$$C_nF_{2n+1} - CH_2 - CH_2 - NR''R''' + R'X \rightarrow [C_nF_{2n+1} - CH_2 - CH_2 - NR'R''R''']^+ -X$$

The new fluorinated products to which the invention is directed have a wide range of uses. They can be used in aqueous solution, in organic solutions or in suspensions as surface active agents in particular as leveling agents in waxes or varnishes. They can be used as emulsifiers for the materials employed as fire extinguishing agents or as emulsifiers of hydrocarbons in aqueous solutions. When added in small amounts to plastics they confer remarkable self-lubricating properties thereto. When adsorbed onto various materials, they give to them oleophobic and hydrophobic properties. Moreover, the products of the invention may be used as germicides.

A few data will indicate the remarkable surface properties of the products of the invention. Thus at concentrations of 1,000 ppm

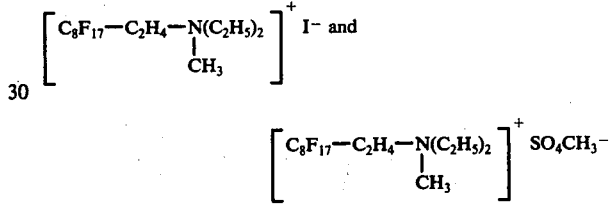

lower the surface tension of water to 19.8 dyne/cm. and 28.3 dyne/cm. at 18° C, respectively. Similarly at a concentration of 800 ppm

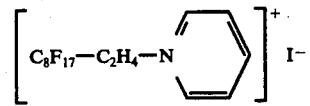

lowers the surface tension of water to 23.3 dyne/cm. The foaming power of the last-mentioned salt is 390, 380 and 370 cm. after 30 seconds, 3 minutes and 5 minutes respectively. The foaming power is measured as the volume of foam obtained after pouring 500 ml of an aqueous solution of the salt, at a temperature of 20° C., onto a surface of the same solution from a height of 450 mm.

The following non-limitative examples illustrate the compounds of the invention. In all of the examples, when a fraction includes several components, the indicated percentages are the molar percentages of the various components and the yields are given with reference to the fluorinated starting materials.

EXAMPLE 1

57.4 grams of $C_8F_{17} - C_2H_4 - I$ in the solid state were gradually added to 79 grams of pyridine heated to 80° C. over a period of 3 hours. The mixture was continuously agitated throughout the reaction. After cooling a solid was recovered by filtering, and this solid was recrystallized in acetone. There were thus recovered 62 grams of

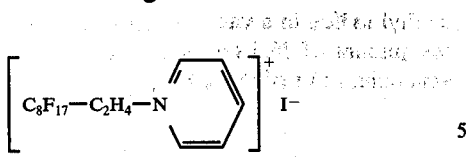

with a transformation yield of 95%. Its analysis, computed for $C_{15}H_9F_{17}NI$, was C 27.6; H 1,4; F 49.5; N 2.1. I 19.4. Found C 27.9; H 1.3; F 49.2; N 2.1; I 19.5.

EXAMPLE 2

31.6 grams of pyridine were added over a three-hour period to 37.4 grams of $C_4F_9-C_2H_4-I$ maintained at 80° C. while maintaining constant agitation. Once the addition was completed the mixture was allowed to stand for 2 hours at 80° C. Upon filtration there were recovered 31.3 grams of a solid A. The filtrate was then distilled and two liquid fractions were recovered:
1. a fraction recovered at 95°-110° C., 3.2 grams in weight, comprised $C_4F_9 - CH = CH_2$ (28.4%, 7.5 mmole) and pyridine (71.6%)
2. a fraction recovered at 115°, amounted to 18.7 grams of pyridine and 12.8 grams of a solid B.

The solids A and B were then mixed and recrystallized in ethyl acetate. There were thus isolated 40.8 grams of

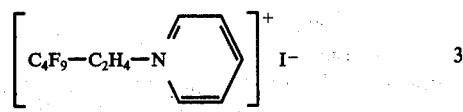

having a melting point between 140° and 144° C. This quaternary ammonium salt was obtained with a transformation yield of 90%. Its analysis computed for $C_{11}H_9F_9NI$ : C 29.1; H 2; F 37.8; N 3.1; I 28; found C 28.7; H 1.9; F 38.1; N 3.2; I 28.1.

EXAMPLE 3

A mixture of 20.1 grams of $C_8F_{17}-C_2H_4-I$ and 45.3 grams of quinoline was heated to 100° C. for 10 hours with continuous agitation. After cooling of the reaction medium there were recovered by filtration 28.3 grams of a solid containing the quinoline and a quaternary ammonium salt, free however from $C_8F_{17}-C_2H_4-I$ which had not entered into the reaction. This solid was crystallized in pyridine and there were recovered 21.4 grams of

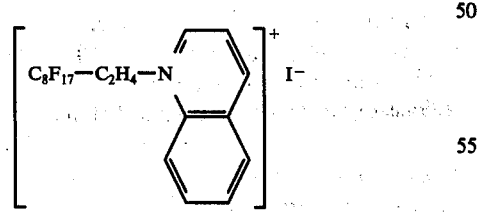

having a melting point of 160°, at which the material underwent decomposition. The transformation yield was 84%. Its analysis, computed for $C_{19}H_{11}F_{17}NI$ : C 32.4; H 1.5; F 46; N 2; I 18.1; found C 31.91; H 1.7; F 45.8; N 2.2; I 18.

EXAMPLE 4

The mixture of 28.7 grams of $C_8F_{17}-C_2H_4-I$ and 46.5 grams of alpha-picoline were heated to 120° for 4 hours with continuous agitation. At the end of the reaction a solid and a filtrate were recovered by filtration. Upon distillation of the filtrate, two fractions were recovered: Fraction<60°/100 mm (2.1 g) consisting of $C_8F_{17} - CH = CH_2$ (91.5%) and α-picoline (8.5%). Fraction 68°-70°/100 mm (38 g) consisting of α-picoline. The solid was recrystallized in acetone, giving 29.8 grams of

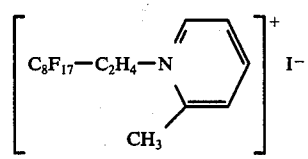

which had a melting point between 205° and 210° at which the material underwent decomposition.

On evaporating off the acetone, there were recovered 3.2 grams of a solid comprising a mixture of

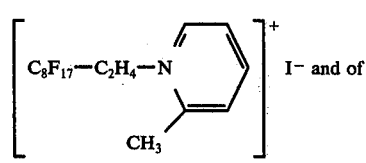 I⁻ and of

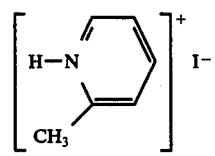

The transformation yield was above 90% The analysis computed for $C_{16}H_{11}F_{17}NI$ : C 28.8 H 1.6; F 48.4; N 2.1; I 19.1; found C 28.6; H 1.7; F 48.1; I 19.3; N 2.3.

Using the same operational methods as those in Examples 1, 2, 3 and 4, there were prepared:

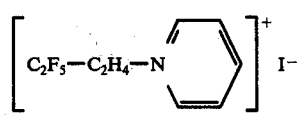

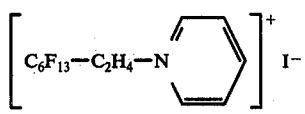

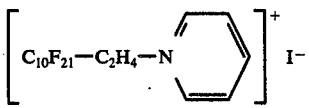

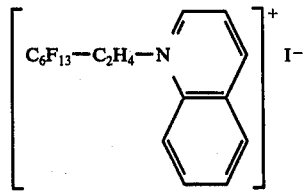

-continued

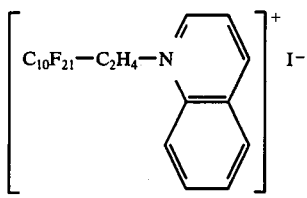

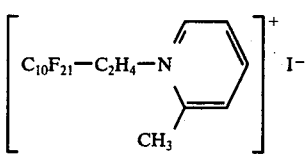

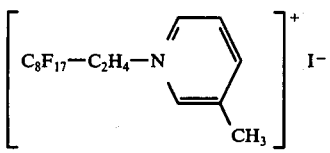

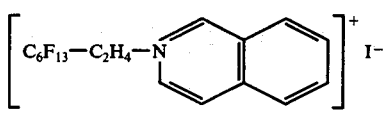

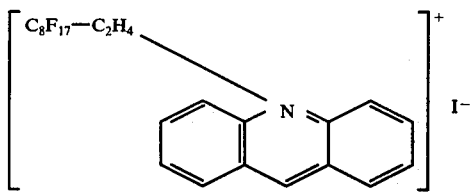

using the iodides of the correspond fluorinated radicals and the aromatic tertiary amines corresponding to the amine remainders as set forth in the above formulas.

EXAMPLE 5

A mixture of 22 grams of $C_8F_{17}-C_2H_4-N(C_2H_5)_2$ and 59.6 grams of methyl iodide were held at 42° for 4 hours with continuous stirring. A white solid appeared in the course of the reaction. After evaporating off the methyl iodide in a vacuum, 27 grams of solid were recovered, this solid was a quaternary ammonium salt of the formula

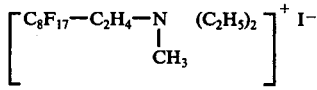

which melts with decomposition between 205° and 215° C. The transformation yield was 97%. The analysis, computed for $C_{15}H_{17}F_{17}NI$; C 27.2; H 2.5; F 49; N 2.1; I 19.2; found C 26.9; H 2.6; F 49.3; N 1.9; I 19.3.

EXAMPLE 6

20.8 grams of

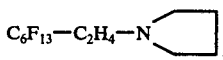

and 71 grams of methyl iodide were heated to 42° for 4 hours with continuous stirring. A white solid appeared during the course of this time. After evaporating off the methyl iodide in a vacuum, the solid was recovered in the amount of 26.5 grams, this solid was a quaternary ammonium salt of the formula

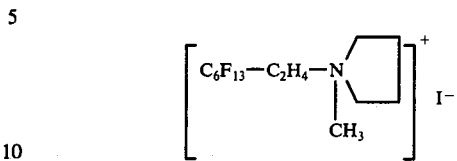

melting, with decomposition, between 195° and 200° C. The formation yield was 95%. Its analysis computed for $C_{13}H_{15}F_{13}NI$ : C 27.9; H 2.7; F 44.2; N 2.5; I 22.7; found C 27.5; H 2.8; F 44.4; N 2.3; 23.

EXAMPLE 7

14.2 grams of methyl iodide were gradually added to 5.59 grams of amine of the formula

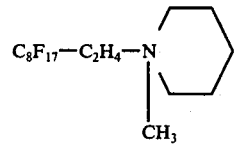

over a period of 30 minutes and continuously stirred with a magnetic stirring device. Once the addition was completed the mixture was held for an hour at 40° C. Thereafter the excess methyl iodide was removed by evaporation in a vacuum, and there was recovered a white solid which was recrystallized in a mixture of ethanol (10% by volume) and ethyl acetate (90% by volume). In this way, there were isolated 6.3 grams of

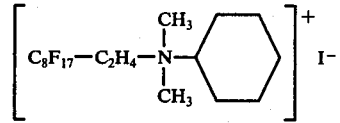

having a melting point between 162° and 164° C. This ammonium quaternary salt was obtained with a transformation yield of 90%. Its analysis computed for $C_{18}H_{21}F_{17}NI$ : C 30.8; H 3.0; F 46.1; N 2.0; I 18.1; found C 30.1; H 3.2; F 46.7; N 2.1; I 17.9. By the same process as that described in Examples 5,6 and 7, the following products were also produced using the tertiary amines and fluorinated iodide compounds corresponding to the radicals or remainders set forth therein:

$[C_8F_{17}-C_2H_4-N(CH_3)_3]^+$ $I^-$ $[C_{12}F_{25}-C_2H_4-N(CH_3)_3]^+$ $I^-$

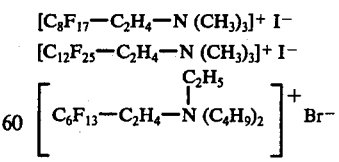

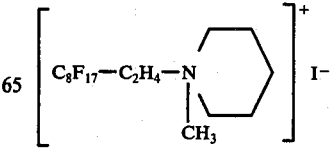

EXAMPLE 8

7.6 grams of $SO_4(CH_3)_2$ were gradually added to 15.6 grams of $C_8F_{17}-C_2H_4-N(C_2H_5)_2$ over a period of 30 minutes. The amine was heated to 65° with the help of a double boiler and was continuously stirred. Over the course of the addition, the temperature rose from 65° to 82° and there appeared a white solid. Once the addition was completed the reaction medium was held at 70° for 30 minutes. Thereafter the reaction medium was agitated with ethyl ether (4 additions of 50 cc.). Upon filtration there were recovered 19 grams of a solid and a filtrate. The ethyl ether was evaporated off from the filtrate and there were recovered 3.4 grams of $SO_4(CH_3)_2$.

The solid was recrystallized in ethyl acetate, yielding 18.1 grams of

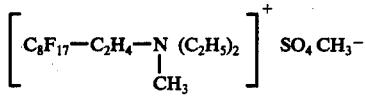

which softened on heating but without exhibiting a definite point of fusion.

The transformation yield was 93%. The analysis, computed for $C_{16}H_{20}F_{17}NO_4S$ : C 30.0; H 2.2; F 50.6; N 2.2; S 5.0. Found C 30.3; H 2.2; F 50.1; N 2.4; S 5.0.

EXAMPLE 9

12.6 grams of $SO_4(CH_3)_2$ were gradually added to 20.8 grams of

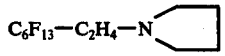

over a period of 30 minutes. The amine was heated to 100° C with the aid of an oil bath and was continuously stirred. During the course of the addition, the temperature of the mixture rose from 100° C to 106° C and there appeared a white solid. After completion of the addition, the reaction medium was held at 100° for 30 minutes. The mix was thereafter agitated with 4 additions of 50 cc. of ethyl ether. On filtering there were recovered 24.9 grams of a solid, and a filtrate. The ethyl ether was evaporated off from the filtrate, giving 5.8 grams of $SO_4(CH_3)_2$. The solid was a quaternary ammonium salt of the formula

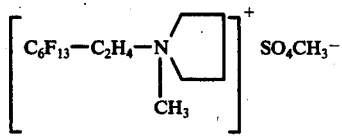

melting between 129° and 132°. The transformation yield was 92%. The analysis computed for $C_{14}H_{18}F_{13}NO_4S$ : C 31; H 3.3; F 45.5; N 2.5; S 5.9; found C 30.6; H 3.1; F 46.0; N 2.7; S 5.8.

EXAMPLE 10

31.5 grams of $SO_4(CH_3)_2$ were added into 22.6 grams of

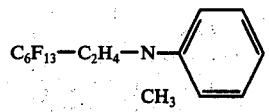

over a period of 30 minutes. The amine was heated to 80° and was continuously agitated. After the end of the addition, the reaction medium was held at 80° for one hour. 25.6 grams of a white solid were then recovered by filtering and this solid was recrystallized in a mixture comprising 10% by volume of ethanol and 90% by volume of ethyl acetate. In this way there was recovered 23.9 grams of

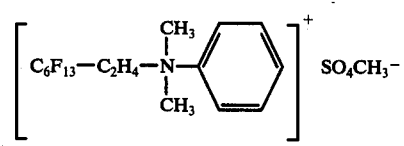

having a melting point between 168° and 170°.

The transformation yield in this case was 93%. The analysis computed for $C_{17}H_{18}F_{13}NO_4S$ : C 35.3; H 3.1; F 42.7; N 2.4; S 5.5. Found C 35.8; H 2.9; F 42.2; N 2.6; S 5.5.

EXAMPLE 11

12.6 grams of $SO_4(CH_3)_2$ were gradually added to 5.59 grams of

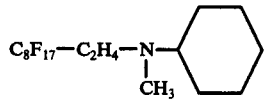

over a period of 30 minutes. The amine was heated to 80° C. and was continuously agitated. The reaction medium was held to 80° for an hour after the end of the addition. By filtration 6.7 grams of a white solid were recovered and this solid was recrystallized in ethyl acetate. There were thus recovered 6.4 grams of

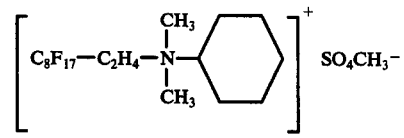

The formation yield was 93% and the analysis computed for $C_{19}H_{24}F_{17}NO_4S$ was C 33.3; H 3.5; F 47.2; N 2.0; S 4.7. Found C 32.9; H 3.7; F 47.6; N 1.9; S 4.6.

We claim:

1. A compound corresponding to the general formula:

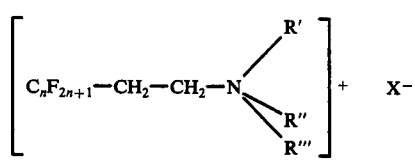

a. $C_nF_{2n+1}$ represents a straight or branched perfluorinated chain with $n$ being between 1 and 20;

b. X⁻ is a halogen, sulfate or an alkyl sulfate; and c. R' is an alkyl radical containing from 1 to 8 atoms of carbons, and R" and R'" together represent a divalent radical linked to the nitrogen by two simple bonds comprising cycloalkyl radicals containing from 4 to 9 carbons, cycloalkenyl radicals containing 4 to 9 carbons, or cyclodienic radicals containing from 4 to 9 carbons.

2. The compound of claim 1 wherein the cycloalkyl radical is N-substituted pyrrolidine.

3. The compound of claim 1 wherein the cycloalkyl radical is N-substituted piperidine.

4. A compound corresponding to the general formula:

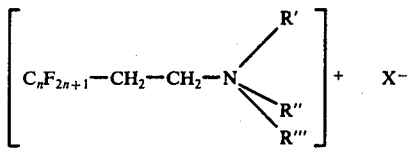

a. $C_nF_{2n+1}$ represents a straight or branched perfluorinated chain with $n$ being between 1 and 20;

b. X⁻ is a halogen, sulfate or an alkyl sulfate; and c. R', R" and R'" make up together and represent N-substituted acridine or N-substituted isoquinoline.

* * * * *

UNITED STATES PATENT AND TRADEMARK OFFICE
CERTIFICATE OF CORRECTION

PATENT NO. : 4,062,849
DATED : December 13, 1977
INVENTOR(S) : Louis Foulletier and Jean-Pierre Lalu It is certified that error appears in the above-identified patent and that said Letters Patent are hereby corrected as shown below:

Column 1, line 5, reads "May 16", should read --May 1--

Column 2, line 39, reads "$+X^{31}$", should read --+X--

Column 5, line 62, reads "C31.91;", should read --C31.9;--

Column 8, line 15, reads "23.", should read --I 23.--

Signed and Sealed this

Fourth Day of April 1978

[SEAL]

Attest:

RUTH C. MASON
Attesting Officer

LUTRELLE F. PARKER
Acting Commissioner of Patents and Trademarks